(12) United States Patent
Leonhard et al.

(10) Patent No.: US 9,408,809 B2
(45) Date of Patent: *Aug. 9, 2016

(54) METHOD FOR PREVENTING THE CRYSTALLIZATION OF PHARMACEUTICALS IN A POLYMER FILM

(71) Applicant: LTS Lohmann Therapie-Systeme AG, Andernach (DE)

(72) Inventors: Johannes Josef Leonhard, Bendorf (DE); Walter Mueller, Andernach (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/056,025

(22) Filed: Oct. 17, 2013

(65) Prior Publication Data

US 2014/0046279 A1    Feb. 13, 2014

Related U.S. Application Data

(63) Continuation of application No. 13/504,970, filed as application No. PCT/EP2010/006535 on Oct. 26, 2010, now Pat. No. 8,932,665.

(30) Foreign Application Priority Data

Nov. 12, 2009 (DE) .......................... 10 2009 052 972

(51) Int. Cl.
   *A61F 13/00* (2006.01)
   *A61K 9/70* (2006.01)
   *A61K 31/381* (2006.01)
   *A61K 9/00* (2006.01)

(52) U.S. Cl.
   CPC ............. *A61K 9/7007* (2013.01); *A61K 9/7023* (2013.01); *A61K 31/381* (2013.01); *A61K 9/006* (2013.01)

(58) Field of Classification Search
   CPC ... A61K 9/006; A61K 9/7038; A61K 9/7007; A61K 9/7084; A61K 31/386
   See application file for complete search history.

(56) References Cited

U.S. PATENT DOCUMENTS

| 4,832,953 | A | 5/1989 | Campbell et al. |
| 5,662,928 | A | 9/1997 | Braun |
| 7,169,409 | B2 | 1/2007 | Dohner et al. |
| 2005/0175678 | A1* | 8/2005 | Breitenbach .................. 424/448 |
| 2008/0226698 | A1* | 9/2008 | Tang et al. .................... 424/448 |
| 2009/0054504 | A1* | 2/2009 | Bozik et al. ................... 514/367 |
| 2009/0197824 | A1* | 8/2009 | Freedman et al. .............. 514/46 |

FOREIGN PATENT DOCUMENTS

| CN | 1671364 | 9/2005 |
| EP | 1 232 151 B1 | 8/2002 |
| EP | 1 669 063 A1 | 6/2006 |
| WO | WO 2004/058247 A1 | 7/2004 |
| WO | WO 2008/146284 A2 | 12/2008 |
| WO | WO 2009/063171 A1 | 5/2009 |
| WO | WO 2010/035111 A1 | 4/2010 |
| WO | WO 2010/073124 A2 | 7/2010 |

* cited by examiner

Primary Examiner — Robert A Wax
Assistant Examiner — Olga V Tcherkasskaya
(74) Attorney, Agent, or Firm — ProPat, L.L.C.

(57) ABSTRACT

The invention relates to a method for preventing the crystallization of a pharmaceutical in a polymer film, wherein the solvent-containing coating compound, which comprises a matrix-forming polymer or polymer mixture and at least one pharmaceutical and is spread to produce the polymer film, is temporarily dried at temperatures that is at least 10° C. above the melting temperature of the pharmaceutical contained in the coating compound. The maximum temperature is thus higher than that which is required for mere drying and obviates the need for an additional, time-consuming and expensive work step.

19 Claims, No Drawings

METHOD FOR PREVENTING THE CRYSTALLIZATION OF PHARMACEUTICALS IN A POLYMER FILM

CROSS-REFERENCE TO RELATED APPLICATIONS

This continuation application claims priority to allowed U.S. patent application Ser. No. 13/504,970, filed Apr. 30, 2012, which claims priority to International Application No. PCT/EP2010/006535, filed Oct. 26, 2010, which claims priority to German Patent Application No. 10 2009 052 972.1, filed Nov. 12, 2009. Each of U.S. patent application Ser. No. 13/504,970; International Application No. PCT/EP2010/006535 and German Patent Application No. 10 2009 052 972.1 are hereby incorporated by reference herein in their entirety.

FIELD OF THE INVENTION

The present invention relates to a method for preventing the spontaneous crystallization of a pharmaceutical in a polymer film. A "spontaneous crystallization" here means a crystallization which takes place without any perceptible stimulus.

BACKGROUND OF THE INVENTION

Transdermal therapeutic systems are administration forms for percutaneous administration of pharmaceuticals. Among transdermal therapeutic systems, a distinction is made between reservoir systems and matrix systems. In the case of the reservoir systems, the pharmaceutical is present in the form of a liquid or semiliquid preparation in a flat reservoir whose wall comprises a membrane via which the pharmaceutical present in the reservoir can be delivered. Matrix systems are distinguished by the fact that the pharmaceutical is present in a polymer film. In their simplest embodiment, matrix systems consist of a pharmaceutical-impermeable backing layer, a pharmaceutical-containing matrix layer, which is usually self-adhesive, and a protective layer which is to be removed before use. However, there are also matrix systems of more complex construction, which may have two or more matrix layers of different compositions, an additional control membrane and/or else non-self-adhesive layers.

Pharmaceutical-containing polymer films are also in use, furthermore, for drugs intended for oral administration, as for example in the form of administration forms in sheet or film form. These drugs for oral administration may be based on a water-soluble polymer, and so the pharmaceutical is released rapidly when the administration form comes into contact with saliva. Water-insoluble or sparingly water-soluble polymers, preferably having mucoadhesive properties, are used for administration forms in sheet or film form with delayed release and/or for transmucosal administration of the pharmaceutical in the oral cavity.

Pharmaceutical-containing polymer films for oral or transdermal therapeutic systems are generally produced by applying a coating material, comprising the matrix-forming polymer or polymer mixture and the pharmaceutical, in a defined thickness to a substrate and then drying it. The coating of the substrate and the drying of the coating take place typically in one continuous operation. Drying in this context generally means the removal of the solvents.

The coating material is a solution or suspension comprising the matrix-forming polymer or the matrix-forming polymer mixture, at least one pharmaceutical, and optionally further excipients, examples being permeation enhancers, plasticizers, flavors, colorants, preservative, antioxidants or the like in a solvent. The solvent is preferably an organic solvent or a mixture of organic solvents.

The pharmaceutical itself may be, but need not be, completely dissolved in the solvent. In those cases where the pharmaceutical is to be fully dissolved in the solvent, there is a risk, even on slight exceedance of the saturation solubility for the pharmaceutical in the coating material, that crystallization nuclei will form in the coating material during coating of the substrate. Within the body of the coating, such crystallization nuclei are able to form as a result of a locally greater evaporation of the solvent or of one solvent component of the solvent mixture, area of a resultant local crystallization of the pharmaceutical.

The local crystallization of the pharmaceutical in the coating material is not a problem if the dried, solvent-free polymer film is subsaturated with pharmaceutical, since under these conditions the crystallization nuclei break up within a short time. The local crystallization of the pharmaceutical in the coating does constitute a problem, however, if she dried polymer film is also supersaturated with pharmaceutical or comprises pharmaceutical in an amorphous modification. Matrix systems supersaturated with pharmaceutical—and this includes systems which comprise the pharmaceutical in an amorphous form—have the advantage of particularly high thermodynamic activity and bioavailability of the pharmaceutical. This advantage, however, is contrasted by the disadvantage that the supersaturated matrix systems are metastable and the bioavailability or the pharmaceutical is severely adversely affected by its crystallization.

In order to prevent the formation of crystalline hydrates of active ingredients liquid at room temperature in a polymeric matrix layer, U.S. Pat. No. 4,832,953 proposed heating the pharmaceutical-containing polymer matrix. Described specifically is the formation of scopolamine hydrate crystals in nonaqueous, polymeric matrices, and an associated, significantly disadvantageous effect on the rate of release of scopolamine from the administration units, in which liquid scopolamine base is present in dispersion in a polyisobutylene/mineral oil matrix. To solve this problem, it is proposed that the ready-packed administration units be heated to 60° C. for a period of 24 hours. This heating of the administration units was sufficient to melt crystals of the scopolamine base hydrate present in the matrix, with a melting point of 59° C., and to prevent formation of crystals after the cooling of the administration units.

With administration units treated in this way, however, the occurrence of additional crystals was observed which had a relatively high melting temperature of 67-70° C. These additional crystals were not eliminated by the heating of the administration units to 60° C. for 24 hours. Nor was it possible to eliminate these additional crystals by raising the temperature to which the packaged administration units were heated. In order to solve this problem, U.S. Pat. No. 5,662,928 proposes heating the scopolamine-containing matrix layer—in addition to the heat treatment of the completed and ready-packaged administration units—to a temperature of between 67° C. and 90° C. for a period of 5 to 15 minutes, immediately prior to lamination with the release-controlling membrane. "Immediately", according to U.S. Pat. No. 5,662,928, means that the lamination must take place within 24 hours, better still within 18 hours, after application of the scopolamine coating.

This known method for preventing crystallization of the pharmaceutical in the polymer matrix has the disadvantage that the matrix layer, after it has been coated, must be further-processed within a short time (24 hours) and can no longer be stored in the interim. This further heat treatment is an additional production step and renders the production method time-consuming and hence also costly.

The object on which the present invention was based was to find a simple and cost-effective way to prevent the crystallization of pharmaceutical in a polymer matrix supersaturated with this pharmaceutical.

SUMMARY OF ADVANTAGEOUS EMBODIMENTS OF THE INVENTION

The object is achieved in a surprisingly simple way by subjecting the coating, which comprises at least the polymer or polymer mixture and the pharmaceutical, to drying, to remove the solvent, at temperatures which at times are at least 10° C. above the melting temperature of the pharmaceutical.

DETAILED DESCRIPTION OF ADVANTAGEOUS EMBODIMENTS OF THE INVENTION

The present invention therefore relates to a method for preventing the crystallization of a pharmaceutical in a pharmaceutical-containing polymer film which in suitable for producing transdermal therapeutic systems or drugs intended for oral administration. A feature of the method is that a substrate is coated with a coating material comprising a solvent or solvent mixture, a matrix-forming polymer or polymer mixture and at least one pharmaceutical, and the solvent or solvent mixture is removed from the coating with application of heat, the maximum temperature during removal of the solvent at times exceeding the melting temperature of the pharmaceutical by at least 10° C. and thus being higher than is necessary for pure drying.

In one preferred embodiment the maximum temperature during the drying of the pharmaceutical-containing coating is at times 10° C. to 25° C. above the melting temperature of the pharmaceutical.

Drying temperatures above 130° C., however, may be problematic, since even heat-resistant polyester films, which are frequently used as a substrate for the coating, begin to soften at these temperatures.

The drying of the pharmaceutical-containing coating ought to take place for at least 1 minute, preferably for at least 1.5 minutes, and more preferably for at least 3 minutes at a temperature which is more than 10° C. above the melting temperature of the pharmaceutical.

The drying of the pharmaceutical-containing coating ought to take place for not longer than 15 minutes, preferably not longer than 10 minutes, and more preferably not longer than 5 minutes at a temperature which is more than 10° C. above the melting temperature of the pharmaceutical.

The pharmaceutical-containing polymer films are typically produced by adding at least one pharmaceutical and optionally further excipients to a solution or suspension of the matrix-forming polymer or polymer mixture. The coating material thus obtained is coated on a sheet like substrate to form a coating having a defined thickness. The coated substrate is then passed through a drying tunnel, in which the solvent or solvent mixture is removed at elevated temperature, leaving only small residual amounts of solvent, not more than 0.5% by weight, in the coating.

In one preferred embodiment the pharmaceutical is dispersed in the form of a solid solution, in the matrix-forming polymer. A "solid solution" is a molecularly disperse distribution of the pharmaceutical in the matrix polymer.

An objective when specifying the drying conditions is to remove the solvent/solvents under extremely gentle conditions. The solvent is selected by the skilled person in dependence on the matrix polymer. The common solvents are heptane, hexane, cyclohexane, ethyl acetate, ethanol, methanol, isopropanol, and tetrahydrofuran.

The matrix-forming polymer itself is not a limiting factor for the method of the invention. Examples of suitable matrix-forming polymers include polysiloxanes, polyacrylates, polyisobutylenes, block copolymers such as styrene-butadiene-styrene block copolymers, and mixtures thereof. Particularly preferred matrix-forming polymers are amine-resistant polysiloxanes.

The matrix-forming polymers are preferably pressure-sensitive adhesive or self-adhesive polymers.

Suitable pharmaceuticals for the method of the invention are active pharmaceutical ingredients which have a melting point of less than 120° C. It is preferred to use active pharmaceutical ingredients whose melting point is below 115° C. Particularly preferred for use are active pharmaceutical ingredients whose melting point is below 105° C. Especially preferred pharmaceuticals are rotigotine and fentanyl.

Example 1

Comparative Example

A two-phase system was produced, with an outer phase comprised of a self-adhesive polysiloxane polymer and an inner phase comprised of a polyvinylpyrrolidone/pharmaceutical complex. The coating material consisted of a dispersion in which the polysiloxane adhesive of the outer phase was present in the solution in n-heptane, and the pharmaceutical, rotigotine, and the polyvinylpyrrolidone of the inner phase were present in solution in ethanol. The pharmaceutical, rotigotine, has a melting temperature of 97-99° C. and the saturation solubility in the coating material is exceeded at room temperature.

The coating was dried in a drying tunnel having the temperature profile indicated in Table 1.

TABLE 1

Comparative Example 1 temperature profile for the drying of the polymer film comprising rotigotine.

| Temperature [° C.] | 40 | 50 | 55 | 60 | 70 | 80 |
|---|---|---|---|---|---|---|
| Time [s] | 50 | 50 | 50 | 50 | 70 | 70 |

The coating operation produced numerous crystallization nuclei within the polymer film, which were not visible immediately after coating. Just 24 hours after its drying, the polymer film exhibited microscopically visible crystallization of the pharmaceutical within the matrix. After 2 days, the crystallization of the pharmaceutical throughout the laminate was evident even to the naked eye.

Example 2

A rotigotine-containing coating material was produced as described in example 1 and was coated in the same way onto a substrate. As a departure from example 1, this coating was dried with the temperature profile indicated in table 2.

TABLE 2

Temperature profile for the drying of a polymer
film comprising rotigotine in accordance with the
method of the invention.

| Temperature [° C.] | 40 | 50 | 60 | 70 | 80 | 90 | 100 | 105 | 115 |
|---|---|---|---|---|---|---|---|---|---|
| Time [s] | 50 | 25 | 25 | 25 | 25 | 25 | 25 | 50 | 100 |

With this drying method, the coating at the end of drying was exposed for a period of just under 3 minutes to a temperature which was above the melting temperature of the pharmaceutical of 97-99° C.

For the pharmaceutical-containing polymer film dried an accordance with the temperature profile indicated in table 2, no crystallization of the pharmaceutical in the polymer matrix could be found even 2 years after coating.

The higher drying temperature with the method according to example 2 has completely prevented the crystallization of rotigotine in the polymer matrix as a consequence of the formation of seed crystals during coating.

That which is claimed:

1. A transdermal therapeutic system or oral administration form comprising a pharmaceutical-containing polymer film, said transdermal therapeutic system or oral administration form formed by a process comprising
   applying a solvent-containing coating material onto a substrate to produce a polymer film, said coating material further comprising a matrix-forming polymer or polymer mixture and at least one pharmaceutical present in dissolved forth and having a melting temperature, and
   drying the coating material,
   wherein said drying step comprises heating, the coated material for at least 1 minute but not longer than 15 minutes at temperatures which are 10° C. to 25° C. above the melting point of the pharmaceutical, said drying step alone preventing crystallization of said pharmaceutical.

2. The transdermal therapeutic system or oral administration form of claim 1, wherein die pharmaceutical has a melting temperature of below 120° C.

3. The transdermal therapeutic system or oral administration form as claimed in claim 2, wherein the pharmaceutical has a melting temperature of below 115° C.

4. The transdermal therapeutic system or oral administration form as claimed in claim 3, wherein the pharmaceutical has a inching temperature of below 105° C.

5. The transdermal therapeutic system or oral administration form of claim 1, wherein the pharmaceutical is selected from the group consisting of rotigotine and fentanyl.

6. The transdermal therapeutic system or oral administration form of claim 1, wherein the pharmaceutical is rotigotine and the drying exposes the coating material to a temperature above the rotigotine melting point for a period of under 3 minutes, eliminating crystallization in the polymer matrix for 2 years.

7. The transdermal therapeutic system or oral administration form as claimed in claim 1, wherein said pharmaceutical is rotigotine in a two-phase polymer mixture.

8. The transdermal therapeutic system or oral administration form of claim 1, wherein the pharmaceutical is dispersed as a solid solution in the matrix-forming polymer.

9. The transdermal therapeutic system or oral administration form of claim 1, wherein the matrix-forming polymer or at least one of the polymers of the matrix-forming polymer mixture is selected from the group consisting of polysiloxanes, polyacrylates, polyisobutylenes, and block copolymers.

10. The transdermal therapeutic system or oral administration form of claim 1, wherein the matrix-forming polymer is an amine-resistant polysiloxane.

11. The transdermal therapeutic system or oral administration form of claim 1, wherein the solvent is selected from the group of organic solvents consisting of heptane, hexane, cyclohexane, ethyl acetate, ethanol, methanol, isopropanol, and tetrahydrofuran.

12. The transdermal therapeutic system or oral administration form of claim 1, wherein the transdermal therapeutic system further comprises a backing layer and a protective layer.

13. The transdermal therapeutic system or oral administration form of claim 1, wherein the matrix-forming polymer further comprises permeation enhancers, plasticizers, flavors, colorants, preservatives or antioxidants.

14. The oral administration form of claim 1, wherein the matrix-forming polymer within the oral administration form is a water-soluble polymer, and said pharmaceutical is rotigotine.

15. The transdermal therapeutic system or oral administration form of claim 1, wherein the oral administration form has delayed release and/or transmucosal administration of the pharmaceutical in the oral cavity.

16. The transdermal therapeutic system or oral administration form of claim 1, wherein the matrix-forming polymer within the oral administration form has mucoadhesive properties.

17. The transdermal therapeutic system or oral administration form of claim 1, wherein said process comprises heating consisting of said drying step and said drying step further consists of drying the solvent-containing coating material on the substrate.

18. The transdermal therapeutic system or oral administration form of claim 1, wherein said polymer film comprises less than 0.5% by weight of residual solvent.

19. Administration forms comprising a supersaturated pharmaceutical-containing polymer film subjected to a process consisting of (i) applying a solvent-containing coating material onto a substrate to produce a polymer film, said caoting material further comprising a matrix-forming polymer or polymer mixture and at least one pharmaceutical present in dissolved form and having a melting temperature, (ii) drying the coating material at temperatures which are 10° C. to 25° C. above the melting temperature of the pharmaceutical present in the coating material for at least one minute but not longer than 15 minutes; (iii) applying an optional protective layer to be removed before use if the administration form is a transdermal therapeutic system; (iv) packaging the administration form prior to administration and (v) administering the administration form, wherein said drying step alone prevents crystallization of said pharmaceutical.

* * * * *